United States Patent [19]

Johnson et al.

[11] Patent Number: 4,709,028

[45] Date of Patent: Nov. 24, 1987

[54] SYNTHESIS OF HETEROCYCLIC AMINES VIA THE REACTION OF DIALKYLENE GLYCOL AND AMMONIA

[75] Inventors: Thomas A. Johnson, Orefield; Cawas A. Cooper, Macungie, both of Pa.

[73] Assignee: Air Products and Chemicals, Inc., Allentown, Pa.

[21] Appl. No.: 10,353

[22] Filed: Feb. 3, 1987

[51] Int. Cl.$^4$ .................. C07D 265/30; C07D 295/02
[52] U.S. Cl. .................................................. 544/106
[58] Field of Search ........................................ 544/106

[56] References Cited

U.S. PATENT DOCUMENTS 4,645,834  2/1987  Dixon et al. ................... 544/106
4,647,663  3/1987  Dixon et al. ................... 544/106

Primary Examiner—Robert W. Ramsuer
Attorney, Agent, or Firm—Russell L. Brewer; James C. Simmons; William F. Marsh

[57] ABSTRACT

This invention relates to an improved process for producing a heterocyclic amine, e.g., morpholine and its derivatives by reacting ammonia and a dialkylene glycol. The improvement resides in adding an inert solvent in the form of an alkyl ether of a polyalkylene glycol with said feed. By including such inert solvent one reduces heavies formation particularly at high conversion.

15 Claims, No Drawings

SYNTHESIS OF HETEROCYCLIC AMINES VIA THE REACTION OF DIALKYLENE GLYCOL AND AMMONIA

TECHNICAL FIELD

This invention relates to the production of heterocyclic amines by the reaction of dialkylene glycol and ammonia. Morpholine, in particular, is synthesized by the reaction of diethlyene glycol and ammonia in the presence of an alkyl ether of polyalkylene glycol.

DESCRIPTION OF THE PRIOR ART

U.S. Pat. No. 2,412,209 discloses a process for producing aliphatic amines from alcohols and particularly morpholine by the reaction of diethylene glycol and ammonia. Temperatures from 160°–400° C. are used and the reaction is carried out in the presence of a hydrogenation catalyst. Examples of hydrogenation catalysts suited for the reaction include Raney nickel, copper chromite, copper-nickel-chromite, iron, cobalt, etc. Liquid or gas phase conditions are suggested.

U.S. Pat. No. 3,154,544 discloses the preparation of substituted morpholines by the vapor phase conversion of a dialkylene glycol having at least one secondary hydroxyl group with hydrogen, and ammonia, in the presence of a hydrogenation/dehydrogenation catalyst. It is noted in the reference that diethylene glycol could not be converted to morpholine by reaction with ammonia in substantial conversion or yield, particularly under conditions suggested in the prior art, e.g. U.S. Pat. Nos. 2,412,209 or 2,529,923.

U.S. Pat. No. 3,155,657 discloses a process for producing polyglycolamines and morpholine by the reaction of diethylene glycol and ammonia. Temperatures of 150°–350° C., pressures of 20–600 atmospheres and a contact time of from 5 minutes to 4 hours are suggested with pressures of 1000–3300 psig being used. The reaction was carried out preferably in the presence of a ruthenium catalyst. Yields of morpholine ranged from about 14–77% with glycol conversions of from about 48–96%.

U.S. Pat. No. 3,151,112 shows a process for producing morpholine and derivatives by the reaction of dialkylene glycols, e.g., diethylene glycol and ammonia at temperatures of 150°–400° C., and pressures of 30–400 atmospheres while maintaining liquid phase conditions. Ammonia is added in large excess to that of stoichiometric requirements. Yields of up to about 50% morpholine at the high reaction pressures are shown.

U.S. Pat. No. 3,151,113 discloses a process of preparing N-alkyl morpholine products by the reaction of a primary or secondary alcohol with morpholine or aminoethoxyethanol in the presence of a hydrogenation catalyst under liquid phase conditions. Pressures of 500–5,000 psig and temperatures of 150°–300° C. are employed. Conventional hydrogenation/dehydrogenation catalysts are used and these may be supported on alumina, kieselguhr, and other various supports or unsupported.

Japanese Patent Publication No. 46-32188, discloses a process for producing morpholine by the reaction of diethylene glycol and ammonia. In carrying out the process, the reactants are charged to an autoclave and reacted at 240° C. and 25 atmospheres in the presence of hydrogen. The improved process relates to the use of a Raney-nickel catalyst having sufficient aluminum therein to consume by-product water as it is produced. The effect of water removal is to extend the catalyst life of the Raney-nickel.

U.S. Pat. No. 4,091,218 discloses a process for recovering ammonia from a gas stream resulting from the catalytic reaction of ammonia and a dialkylene glycol as described in U.S. Pat. No. 3,151,112. In the process, the recovery of the product is effected by contacting the reaction effluent gas stream containing unreacted hydrogen, ammonia, and methane with a dialkylene glycol feedstock under conditions for adsorbing ammonia and leaving anhydrous hydrogen and methane.

British Pat. No. 1,530,570 discloses a process for producing 2-(2-aminoalkoxy)alkanol and morpholine derivatives from ammonia and oxydialkanol under pressures sufficient to maintain liquid conditions. Temperature and pressure are controlled in order to vary the quantity of the 2-(2-aminoalkoxy)alkanol and morpholine derivative produced. Temperatures generally are 200°–220° C. while gauge pressures of at least 700 psig are used. Ammonia to alkanol ratios of 6:1 are used, with the ammonia being in the anhydrous form. Hydrogen is added to maintain catalyst activity.

SUMMARY OF THE INVENTION

This invention relates to an improved process for forming heterocyclic amines particularly in the form of morpholine and its derivatives. The basic process comprises reacting a dialkylene glycol or dialkylene glycolamine and ammonia in the presence of hydrogen and a hydrogenation/dehydrogenation catalyst at conventional temperatures by continuously charging the reactants to a trickle-bed catalytic reactor and operating the reactor under conditions such that the dialkylene glycol is present as a discontinuous liquid phase and the heterocyclic amine is predominantly in the gas phase. The improvement resides in carrying out the reaction in the presence of a dialkyl ether of a polyalkylene glycol of the formula:

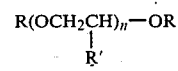

where R is methyl or ethyl and R' is hydrogen, methyl or ethyl and n is 2–6.

Several advantages are associated with the improved process of this invention as compared to the prior art. These include:

the reaction conditions are moderate, e.g., low pressures are used thereby resulting in an energy saving as compared to prior art processes operating under high pressure, liquid phase conditions; and high selectivity to the heterocyclic amine, i.e. morpholine and its derivatives and reduced amounts of heavies in the form of polyamines, e.g., morpholino diethylene glycol (MDEG), bis-morpholino diethylene glycol (BMDEG) and bis-diethyleneglycolamine is achieved.

DESCRIPTION OF THE PREFERRED EMBODIMENTS

The feed component suited for practicing the process is a dialkylene glycol or dialkylene glycolamine of the formula:

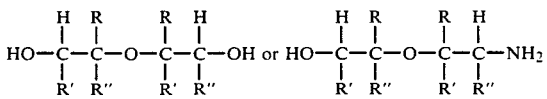

where R, R', and R" may be identified or different, each representing a hydrogen atom, alkyl or phenyl radicals. R, R', and R" contain typically from 1 to 6 carbon atoms, if alkyl, and preferably not more than 2 carbon atoms. For purposes of producing a commercially important heterocyclic amine, i.e. morpholine, the dialkylene glycol is diethylene glycol (DEG). Others, result in the production of alkyl and phenyl substituted morpholine derivatives. Specific examples of preferred dialkylene glycols and dialkylene glycolamines include diethylene glycol, dipropylene glycol, dibutylene glycol, diethyleneglycolamine (2-aminoethoxyethanol), etc.

As with other processes, the reaction of dialkylene glycol or dialkylene glycolamine to form heterocyclic amines is carried out in the presence of ammonia. Ammonia to dialkylene glycol ratios, on a molar basis, are at least 1:1 and up to 100:1, but preferably 4 to 16:1. While the process requires at least equal molar amounts of ammonia to glycol or glycolamine to permit reaction on a stoichiometric basis, molar ratios higher than about 16 to 20:1 do not result in significant advantages. Because of the unique nature of the reaction conditions for carrying out the process, higher ratios of ammonia to glycol can have a detrimental effect in commercial units in that such higher ratios require increased pressures.

The presence of hydrogen is necessary for the proper and efficient conduct of the process. It is used in combination with ammonia and it is believed its function is to maintain catalyst activity. Molar ratios of ammonia to hydrogen generally are from about 4 to 60:1 and preferably about 6 to 32:1. Low ratios of ammonia to hydrogen, e.g., 2:1 to about 4:1 generally result in increased heavies formation. It is believed lower ammonia to hydrogen ratios reduce the ammonia content in the liquid phase thereby permitting any residual liquid phase morpholine to react and form heavies. Such is also true with the introduction of other inert gases such as nitrogen or methane. They, like hydrogen, reduce the ammonia content in the liquid phase. Therefore, it is preferred to use the minimum amount of hydrogen necessary to maintain the catalyst in the reactive state.

The catalysts suited for practicing the invention include those commonly used in prior art processes provided that they are wettable with the dialkylene glycol or dialkylene glycolamine under the reaction conditions. By wettable, it is meant the catalyst will permit the formation of a very thin, liquid film about the surface of the catalyst as required in a trickle bed. The hydrogenation/dehydrogenation catalysts suited for practicing the process generally includes one or more metals from the group consisting of copper, nickel, cobalt, chromium, molybdenum, manganese, platinum, palladium, ruthenium, and rhodium. The preferred catalysts, i.e. those which are most effective for the reactant are nickel, cobalt and copper or contain such components.

Most of the above hydrogenation/dehydrogenation metals, even in highly porous form, will not permit the formation of thin film of dialkylene glycol about its surface, but rather will cause it to bead up on the surface. In those cases, the metal should be impregnated or incorporated into a wettable support. The support for the hydrogenation-dehydrogenation catalyst then is (a) one which is inert to the extent that it is not soluble or reactable with the reaction medium and (b) one which is wettable by the dialkylene glycol or dialkylene glycolamine. Supports suited include silica, alumina, kieselguhr, and others conventionally used in the art. Alumina and silica are preferred. Broadly, the proportion of hydrogenation/dehydrogenation metal by weight of the catalyst, including support, is from about 0.01% to 70% and typically between 20 to 40%. This level may vary to the extent the catalyst loses its wettability.

In practicing the process, the temperature and pressure are maintained in the catalytic reaction zone such that some, at least about 1 mole percent preferably at least 5 mole percent, of the reactant dialkylene glycol is in the liquid phase, while the heterocyclic product is predominately in the vapor phase, e.g. greater than 80 mole percent, and preferably 90%, assuming 90% conversion of the dialkylene glycol and 75% of the intermediate if one is formed. In addition, the temperature and pressure are selected so the reaction conditions do not substantially exceed (greater than about 10° C.) the dew point temperature of the feed.

In the practice of this invention, a dialkyl ether of a polyalkylene glycol is incorporated with the feed dialkylene glycol or dialkylene glycol amine. The dialkyl ether of the polyalkylene glycol is represented by the formula below:

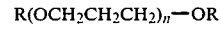

where R is methyl or ethyl and R' is hydrogen, methyl or ethyl and n is 2–6. The methyl and ethyl ethers of glycerol are also suitable solvents.

The dialkyl ethers of polyalkylene glycols are inert to the reaction conditions and miscible with the other components of the reaction mixture, e.g., both reactants and reaction product. Examples of suitable alkyl ethers of polyalkylene glycols, and preferably polyethylene glycols include the dimethyl ether of diethylene glycol, the dimethyl ether of triethylene glycol and the dimethyl ether of tetraethylene glycol.

The dialkyl ethers of polyalkylene glycols are added to the feed on a weight basis of about 30 to 80% by weight of the dialkylene glycol or dialkylene glycol amine, and preferably from 40 to 60% by weight of the dialkylene glycol or dialkylene glycol amine. As the concentration of the dialkylene glycol or dialkylene glycol amine is increased in the feed, e.g., above 80%, the percentage of heavies produced in the reaction, particularly at high conversion of the dialkylene glycol to heterocyclic amine, increases. The addition of the dialkyl ether of the polyalkylene glycols decreases the production of heavies, particularly at the high levels of conversion, e.g., 95% and above. In other words, selectivity is enhanced at a comparable conversion by the addition of the dialkyl ether of the polyalkylene glycol.

To permit the maintenance of an appropriate contact time in the reaction zone for the conversion of dialkylene glycol to the heterocyclic amine, the reaction is generally carried out at a liquid hourly space velocity of from 0.05 to 2.5 hr.$^{-1}$. (Liquid hourly space velocity (LHSV) is defined as the ratio of the volume of liquid dialkylene glycol per volume of catalyst per hour.) The liquid hourly space velocity is not as critical as some other parameters in the process in that it is largely dependent upon the activity of the catalyst. In those instances where the catalyst is highly reactive, a higher liquid hourly space velocity can be utilized to achieve greater throughput. Alternatively, where a catalyst having lower activity is used, lower space velocities are employed. Generally, liquid hourly space velocity is adjusted to permit the greatest conversion based on desired throughput. Commercially, it is possible to operate at a lower conversion and obtain greater product yield in view of the increased throughput through the reactor. Of course this will result in increasing the amount of by-product material coming from the reactor that must be recycled or recovered. A preferred LHSV range for cobalt or nickel containing catalysts is from about 0.2 to 1.0 hr.$^{-1}$.

The pressure used for the reaction is adjusted to meet desired vapor-liquid criteria for the reactants and products. In addition, the pressure must be adjusted to provide for a desired rate of reaction. Pressures generally suited for commercial operation are from 125 to 500 psig. However, pressures generally higher than 300 are not used as they show no significant improvement in the trickle bed reactor. Pressures above about 500 psig can result in increased heavies formation. Preferred pressures are about 200-300 psig.

The temperature used for carrying out the reaction generally is from about 140° to 280° C. at the pressure range specified. Of course as the pressure is increased, temperatures can be increased to the extent the vapor-liquid equilibrium criteria is met. Typically, the temperature used is from 180° to 250° C. Higher temperatures often cause coking of the catalyst or deactivation.

EXAMPLE 1

A tubular reaction (½″ OD) system was charged with 16 cc of 43% nickel oxide on alumina catalyst. This catalyst was reduced with hydrogen and then diethylene glycol (DEG 4 ml/hr), ammonia (9.6 ml/hr) and hydrogen (7.87 sccm) were introduced at 190° C. and 300 psig downflow through the reactor. The mole ratio DEG/NH$_3$/H$_2$ was 1/8/0.5 After this 6-day pretreatment, DEG flow was stopped and a tetraglyme solution containing 22% (by wt) diethylene glycolamine (DEGA) was fed at 2 ml/hr. The ammonia flow was increased to 12 ml/hr while keeping the hydrogen flow constant. The mole ratio of DEGA/NH$_3$/H$_2$ was 1/100/5. A sample collected over a period of 24 hours was analyzed by gas chromatography (GC) after cooling to room temperature. The GC analysis of the sample indicated that all DEGA was converted and the main product was MOR (see Table I). Molar selectivity to MOR was 84%.

EXAMPLE 2

The procedure of Example 1 was repeated except that a tetraglyme solution containing 40% DEGA (by wt) was fed through the reactor at 2 ml/hr after checking catalyst activity. Ammonia and hydrogen flows were 12 ml/hr and 7.87 sccm. The mole ratio DEGA/NH$_3$/H$_2$ was 1/50/2.5. Samples collected over a period of 24 hours at 200° C. were analyzed by GC after cooling to room temperature. The GC analysis indicated that DEGA conversion was 95% and the majority of the product was still morpholine (see Table I). Molar selectivity to MOR was 79%.

EXAMPLE 3

The procedure of Example 2 was repeated except that the DEGA concentration in tetraglyme was increased to 60%. The DEGA/tetraglyme solution, ammonia and hydrogen flow rates were 2 ml/hr, 12 ml/hr, and 7.87 sccm. The mole ratio DEGA/NH$_3$/H$_2$ was 1/30/1.5. Samples from this experiment were cooled to room temperature and analyzed on the GC. Results showed DEGA conversion of 92% and molar selectivity to MOR was 76% (see Table I).

EXAMPLE 4

The procedure of Example 3 was repeated except that the DEGA (by wt) in tetraglyme was 80%. Flow rates and sample analysis were similar. The GC results showed 85% DEGA conversion and 72% molar selectivity to MOR (see Table I).

EXAMPLE 5

The procedure of Example 4 was repeated in order to complete the series of experiments except that this reaction was run without any tetraglyme in the feed. Flow rates of DEGA, ammonia, and hydrogen were 2 ml/hr, 12 ml/hr, and 7.87 sccm. The mole ratio DEGA/NH$_3$/H$_2$ was 1/15/0.8. Samples were analyzed on GC after cooling to room temperature. Without dilution DEGA conversions of 73% and 61% molar selectivity to morpholine were observed (see Table I).

EXAMPLE 6

The procedure of Example 1 was repeated except that fresh catalyst was used but loaded, reduced, and pretreated as described in Example 1. The reactor system and conditions were identical except the operating pressure was 250 psig. After pretreatment, a tetraglyme solution containing 60% (by wt) diethylene glycol (DEG) was fed through the reactor at 2 ml/hr. The mole ratio DEG/NH$_3$/H$_2$ was 1/36/1.8. Ammonia flow was increased to 12 ml/hr keeping hydrogen flow constant. Samples were collected, cooled to room temperature, and analyzed on the GC. Results showed 99.5% DEG conversion and 66% molar selectivity to morpholine in the products (see Table II).

EXAMPLE 7

The procedure of Example 6 was repeated after a catalyst activity check, except that the DEG concentration in tetraglyme was increased to 80% (by wt). The DEG/tetraglyme solution, ammonia, and hydrogen flow rates were 2 ml/hr, 12 ml/hr, and 7.87 sccm. The mole ratio DEG/NH$_3$/H$_2$ was 1/26/1.3. The GC analysis of samples cooled to room temperature showed 99.4% DEG conversion and 53% molar selectivity to morpholine (see Table II).

EXAMPLE 8

The procedure of Example 7 was repeated except that DEG was fed over the catalyst at a flow rate of 2 ml/hr keeping ammonia and hydrogen flow constant. The mole ratio DEG/NH$_3$/H$_2$ was 1/20/1. Samples were analyzed on GC and results show 96.3% DEG conversion and 47% molar selectivity to morpholine (see Table II).

TABLE I[a]

| EX | DEGA in TETRA-GLYME (%) | WATER | LIGHTS[b] | MOR[c] | MEDIUMS[d] | DEGA[e] | HEAVIES[f] | TETRA-GLYME | CON-VERSION[g] | SELECT-IVITY[h] |
|---|---|---|---|---|---|---|---|---|---|---|
| 1 | 22 | 4.08 | 0.04 | 15.30 | 0.94 | 0 | 1.33 | 78.30 | 100 | 84 |
| 2 | 40 | 7.88 | 0.68 | 24.74 | 0.54 | 2.17 | 3.66 | 60.31 | 95 | 79 |
| 3 | 60 | 9.33 | 1.43 | 34.65 | 1.49 | 4.92 | 7.92 | 40.26 | 92 | 76 |
| 4 | 80 | 11.17 | 0.10 | 40.40 | 1.26 | 12.02 | 14.93 | 20.16 | 85 | 72 |
| 5 | 100 | 11.13 | 0.30 | 36.92 | 2.34 | 27.46 | 21.82 | 0 | 73 | 61 |

[a] Ammonia free normalized weight percent of components in product.
[b] Ethyl morpholine, methoxy ethanol, and any unknowns eluting before morpholine.
[c] Morpholine
[d] Methoxyethyl morpholine, ethylene glycol, aminoethyl morpholine, hydroxyethyl morpholine and any unknowns eluting between MOR and DEG.
[e] Diethylene Glycolamine
[f] Morpholineodiethylene glycol, morpholinone, bis-morpholinodiethylene glycol, bis-diglycolamine, any unknowns eluting after DEG, and non-eluting compounds.
[g] DEGA conversion (%) based on GC analysis.
[h] Molar selectivity (%) to morpholine.

The above results show that the addition of tetraglyme reduces the amount of heavies in the conversion of diethylene glycolamine to morpholine and particularly at high conversion.

TABLE II[a]

| EX | DEG in TETRA-GLYME (%) | WATER | LIGHTS[b] | MOR[c] | MEDIUMS[d] | DEGA[e] | DEG[f] | HEAVIES[g] | TETRA-GLYME | CON-VERSION[h] | COMBINED[i] SELECTIVITY | MORPHOLINE[j] SELECTIVITY |
|---|---|---|---|---|---|---|---|---|---|---|---|---|
| 6 | 60 | 15.82 | 1.42 | 32.39 | 0.94 | 4.50 | 0.30 | 4.20 | 40.44 | 99.5 | 74 | 66 |
| 7 | 80 | 19.03 | 1.78 | 34.85 | 1.18 | 10.82 | 0.54 | 11.09 | 20.71 | 99.4 | 67 | 53 |
| 8 | 100 | 25.39 | 4.38 | 44.00 | 1.14 | 5.14 | 3.66 | 16.29 | 0 | 96.3 | 75 | 47 |

[a] Ammonia free normalized weight percent of components in product.
[b] Ethyl morpholine, methoxy ethanol, and any unknowns eluting before morpholine.
[c] Morpholine
[d] Methoxyethyl morpholine, ethylene glycol, aminoethyl morpholine, hydroxyethyl morpholine and any unknowns eluting between MOR and DEG.
[e] Diethylene Glycolamine
[f] Diethylene Glycol
[g] Morpholinodiethylene glycol, morpholine, bis-morpholinodiethylene glycol, bis-diglycolamine, any unknowns eluting after DEG, and non-eluting compounds.
[h] DEG conversion (%) based on GC analysis.
[i] Molar selectivity (%) to morpholine and DEGA.
[j] Molar selectivity (%) to morpholine.

The above results show that as the concentration of diethyleneglycol is increased in the feed solution, the percent heavies increases at the conversion levels shown.

What we claim is:

1. In a process for producing a heterocyclic amine by the reaction of a dialkylene glycol or dialkylene glycolamine of the formula:

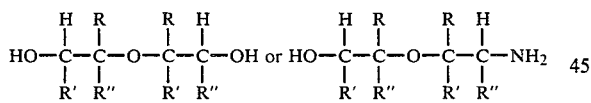

where R, R', and R", may be identical or different, each representing a hydrogen atom, alkyl or phenyl radicals, and ammonia in a fixed bed catalytic reactor, said reaction being carried out in the presence of hydrogen and a hydrogenation-dehydrogenation catalyst wherein at least 1 mole percent of said dialkylene glycol or dialkylene glycolamine is maintained in the liquid phase; said dialkylene glycol or dialkylene glycolamine and ammonia being passed downflow through said reactor at a rate such that the dialkylene glycol is present in said reactor as a discontinuous phase, and the heterocyclic amine formed during the reaction is predominantly in the vapor phase; and
   continuously removing heterocyclic amine product from the reactor; the improvement which comprises:
   introducing said dialkylene glycol or dialkylene glycolamine or a solution containing from about 30–80% by weight of said dialkylene glycol or dialkylene glycolamine in a dialkyl ether of a polyalkylene glycol of the formula:

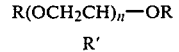

$R(OCH_2CH_2CH_2)_n$—OR and $R(OCH_2CH_2CH_2)_nOR$ where R is methyl or ethyl and R' is hydrogen, methyl or ethyl and n is 2–6 to said fixed bed catalytic reactor.

2. The process of claim 1 wherein said dialkylene glycol is diethylene glycol.

3. The process of claim 2 wherein the temperature maintained in the reactor is from about 140° to 280° C.

4. The process of claim 3 wherein the pressure maintained in the reactor is from about 125 to 500 psig.

5. The process of claim 4 wherein the liquid hourly space velocity, based on dialkylene glycol feed, is from about 0.05 to 2.5.

6. The process of claim 5 wherein the hydrogenation-dehydrogenation catalyst is wettable by the dialkylene glycol and is carried on a support selected from the group consisting of alumina and silica.

7. The process of claim 6 wherein said hydrogenation-dehydrogenation catalyst carried upon the support contains a component selected from the group consisting of nickel, cobalt and chromium.

8. The process of claim 7 wherein said hydrogenation-dehydrogenation catalyst is a nickel catalyst supported on alumina.

9. The process of claim 5 wherein said reaction zone is maintained at about 200–300 psig.

10. The process of claim 9 wherein the ammonia to hydrogen ratio is from 6-32:1, and the ratio of ammonia to diethylene glycol is from 4-16:1.

11. The process of claim 10 wherein said dialkyl ether of a polyalkylene glycol is the dimethyl ether of tetraethylene glycol.

12. The process of claim 1 wherein the reactant is diethylene glycol amine.

13. The process of claim 12 wherein the temperature is maintained from 140°-280° C., pressure from 125 to 500 psig and said dialkylether is the dimethyl ether of tetraethylene glycol.

14. In a process for producing morpholine by the reaction of a feed comprising diethylene glycol and ammonia in a reactor, said reaction being carried out in the presence of hydrogen and a hydrogenation-dehydrogenation catalyst;

passing said ammonia and diethylene glycol downflow through a tubular reactor packed with said hydrogenation/dehydrogenation catalyst, said passing being at a rate to provide a liquid hourly space velocity, based on diethylene glycol, of 0.5-2.5 hours$^{-1}$;

establishing a mole ratio of ammonia to hydrogen from 6-32:1 and an ammonia to diethylene glycol ratio of about 4-16:1 in said reactor;

operating the reactor within a temperature range of 140°-280° C. and a pressure range of from 125-500 psig, such temperature and pressure being controlled within such range that at least 5% of the diethylene glycol is in the liquid phase; and removing morpholine product from the reactor;

the improvement which comprises:

introducing a solution containing dimethyl ether of tetraethylene glycol solvent and from 40-60% by weight diethylene glycol solute as said feed to said reactor.

15. The process of claim 13 wherein the hydrogenation-dehydrogenation catalyst is carried on a support selected from the group consisting of alumina, silica and mixtures thereof and the support contains a component selected from the group consisting of nickel, cobalt and chromium.

* * * * *